(12) United States Patent
Lamb

(10) Patent No.: US 10,898,639 B1
(45) Date of Patent: Jan. 26, 2021

(54) PORTABLE ENTERAL FEEDING PLATFORM

(71) Applicant: Terrill Lamb, Gautier, MS (US)

(72) Inventor: Terrill Lamb, Gautier, MS (US)

( * ) Notice: Subject to any disclaimer, the term of this patent is extended or adjusted under 35 U.S.C. 154(b) by 313 days.

(21) Appl. No.: 16/111,462

(22) Filed: Aug. 24, 2018

(51) Int. Cl.
*F16M 13/00* (2006.01)
*A61M 5/14* (2006.01)
*A61J 15/00* (2006.01)
*A61M 5/00* (2006.01)
*F16M 13/02* (2006.01)
*F16L 3/08* (2006.01)

(52) U.S. Cl.
CPC ........ *A61M 5/1415* (2013.01); *A61J 15/0053* (2013.01); *A61M 5/008* (2013.01); *A61M 5/1418* (2013.01); *A61M 2209/084* (2013.01); *F16L 3/08* (2013.01); *F16M 13/022* (2013.01)

(58) Field of Classification Search
CPC .............. A61M 5/1414; A61M 5/1415; A61M 5/1417; A61M 5/1418
See application file for complete search history.

(56) References Cited

U.S. PATENT DOCUMENTS

| | | |
|---|---|---|
| 4,713,064 A | 12/1987 | Bruno et al. |
| 4,986,158 A * | 1/1991 | Johnson ................. F16M 11/22 84/327 |
| 5,386,958 A | 2/1995 | Amato |
| D373,823 S | 9/1996 | Baldwin |
| 6,135,983 A | 10/2000 | Andrews et al. |
| 6,280,422 B1 | 8/2001 | Sanchez-Browning |
| 6,464,188 B1 | 10/2002 | Donovan |
| 6,471,167 B1 * | 10/2002 | Myers .................. A61G 13/101 248/125.9 |
| D622,377 S | 8/2010 | Jackson |
| D710,994 S | 8/2014 | Yazbeck |
| 9,436,222 B2 * | 9/2016 | Lee ....................... G06F 1/1633 |
| 9,642,778 B1 | 5/2017 | Yazbeck |
| 2004/0262463 A1 | 12/2004 | Jackson |
| 2008/0076654 A1 * | 3/2008 | Riga .................... B31D 5/0047 493/464 |
| 2010/0057017 A1 | 3/2010 | Pappas et al. |
| 2017/0309262 A1 * | 10/2017 | Walker ................... F16M 11/28 |
| 2018/0049951 A1 * | 2/2018 | Hunter ................... A47L 13/16 |

* cited by examiner

*Primary Examiner* — Steven M Marsh
(74) *Attorney, Agent, or Firm* — George L Williamson

(57) ABSTRACT

Method and apparatus for a portable enteral feeding platform having a telescoping two-piece upright column support which is height adjustable, being pivotally mounted onto a base so that the upright column can be pivoted forwardly onto the base into a storage position. In the upright position, the upright column support is both height adjustable and 360 degrees rotatable at its top where it supports an adjustable clamp wherein the clamp can be rotated 360 degrees and locked in place and wherein the adjustable clamp can be moved toward and away from the upright support column to a user selected position. The adjustable clamp is designed to receive and securely hold a syringe or like feeding tube. An optional base clamp is also provided for securing the base to a table top or like support surface.

20 Claims, 5 Drawing Sheets

PORTABLE ENTERAL FEEDING PLATFORM

BACKGROUND OF THE INVENTION

Field of the Invention

The present invention relates generally to medical devices and, more particularly, is concerned with a portable enteral feeding system for patients requiring enteral feeding and by persons with feeding tubes placed for medical reasons.

Enteral tube feeding (ETF) is used to feed patients who cannot attain an adequate oral intake from food and/or oral nutritional supplements, or who cannot eat/drink safely. Since its introduction in the early 1980s, percutaneous endoscopic gastrostomy (PEG) tubes are increasingly being placed among elderly individuals as an alternative to nasogastric tubes and surgically placed gastrostomy tubes. While only 15,000 PEG tubes were placed in 1989, its placement frequency had increased significantly to 216,000 tubes by the year 2000, and this trend is projected to continue, especially in elderly patients with cognitive impairment.

From 1993 to 2003, according to a study published in the U.S. National Library of Medicine, the number of enteral tube placements in elderly patients with dementia increased by 38% and continues to grow.

Increasing prevalence of cancer is also one of the key factors leading to the growth of the market for enteral feeding formulas. Ensuring nutritional support during cancer therapy is of utmost importance. Patient recovery during chemotherapy, pre-surgery, and post-surgery is greatly affected by patient diet and nutrition; therefore, oncology is the largest application area for the enteral feeding formulas market.

While the use of ETF has improved the nutritional outcomes for people at risk for medical related malnourishment, the related mental and social aspects of EFT use has been greatly ignored. The present invention is designed to provide portability and stability in an aesthetically acceptable manner, allowing ETF users to comfortably share in the social aspects of eating, both at home and in public.

Description of the Related Art

Devices relevant to the present invention have been described in the related art, however, none of the related art devices disclose the unique features of the present invention.

In U.S. Pat. No. 6,280,422 dated Aug. 28, 2001, Sanchez-Browning disclosed a feeding apparatus with replaceable feeding bottle. In U.S. Pat. No. 5,386,958 dated Feb. 7, 1995, Amato disclosed a feeding tube support apparatus. In U.S. Pat. No. 6,135,983 dated Oct. 24, 2000, Andrews, et al., disclosed a gastric tube feeding system. In U.S. Pat. No. 6,464,188 dated Oct. 15, 2002, Donovan disclosed a nutrient feeding support apparatus. In U.S. Pat. No. 9,642,778 dated May 9, 2017, Yazbeck disclosed a feeding tube holder. In U.S. Pat. No. 4,713,064 dated Dec. 15, 1987, Bruno, et al., disclosed an enteral feeding device. In U.S. Patent Application Publication No. 2004/0262463 dated Dec. 30, 2004, Jackson disclosed an adjustable support device for a feeding tube. In U.S. Patent Application Publication No. 2010/0057017 dated Mar. 4, 2010, Pappas, et al., disclosed a feeding syringe assembly for an endoscopic gastronomy tube. In U.S. Pat. No. D 373,823 dated Sep. 17, 1996, Baldwin disclosed a gastrointestinal tube syringe holder. In U.S. Pat. No. D 622,377 dated Aug. 24, 2010, Jackson disclosed a support stand for a feeding tube. In U.S. Pat. No. D 710,994 dated Aug. 12, 2014, Yazbeck disclosed a feeding tube holder.

While these devices may be suitable for the purposes for which they were designed, they would not be as suitable for the purposes of the present invention as hereinafter described. As will be shown by way of explanation and drawings, the present invention works in a novel manner and differently from the related art.

SUMMARY OF THE PRESENT INVENTION

The present invention discloses a portable enteral feeding platform having a telescoping two-piece upright column support which is height adjustable, being pivotally mounted onto a base so that the upright column can be pivoted forwardly onto the base into a storage position. In the upright position, the upright column support is both height adjustable and 360 degrees rotatable at its top where it supports an adjustable clamp wherein the clamp can be rotated 360 degrees and locked in place and wherein the adjustable clamp can be moved toward and away from the upright support column to a user selected position. The adjustable clamp is designed to receive and securely hold a syringe or like feeding tube for use with the enteral feeding system of the present invention. An optional base clamp is also provided for securing the base to a table top or like support surface.

An object of the present invention is to provide an enteral feeding system which is portable. A further object of the present invention is to provide an enteral feeding system which can be folded into a storable position so that it can be easily transported from one place to the next. A further object of the present invention is to provide an enteral feeding system which can be easily operated by a user. A further object of the present invention is to provide an enteral feeding system which can be relatively easily and inexpensively manufactured.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
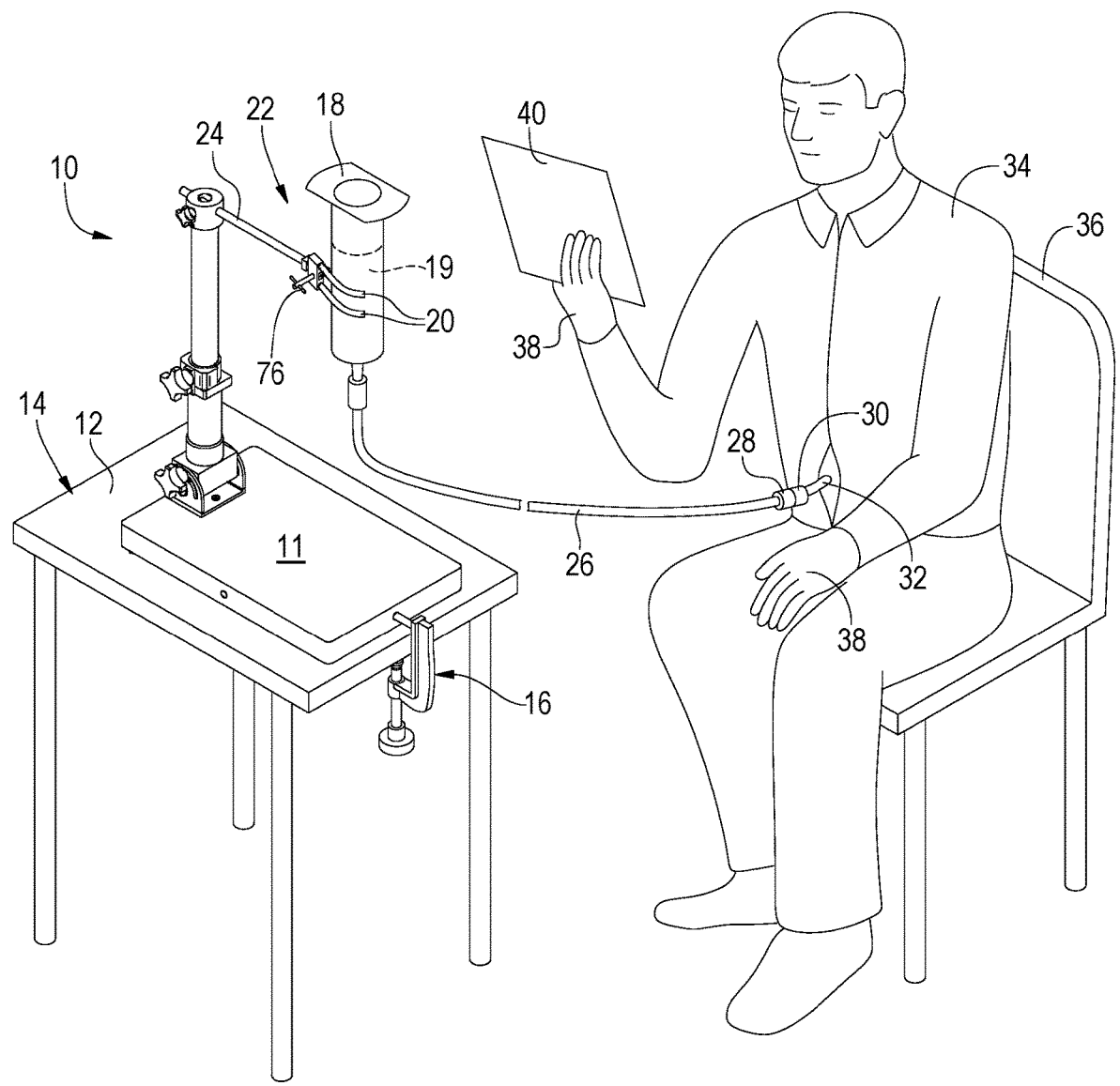
FIG. 1 is a perspective view of the present invention shown in operative connection.
Figure 2:
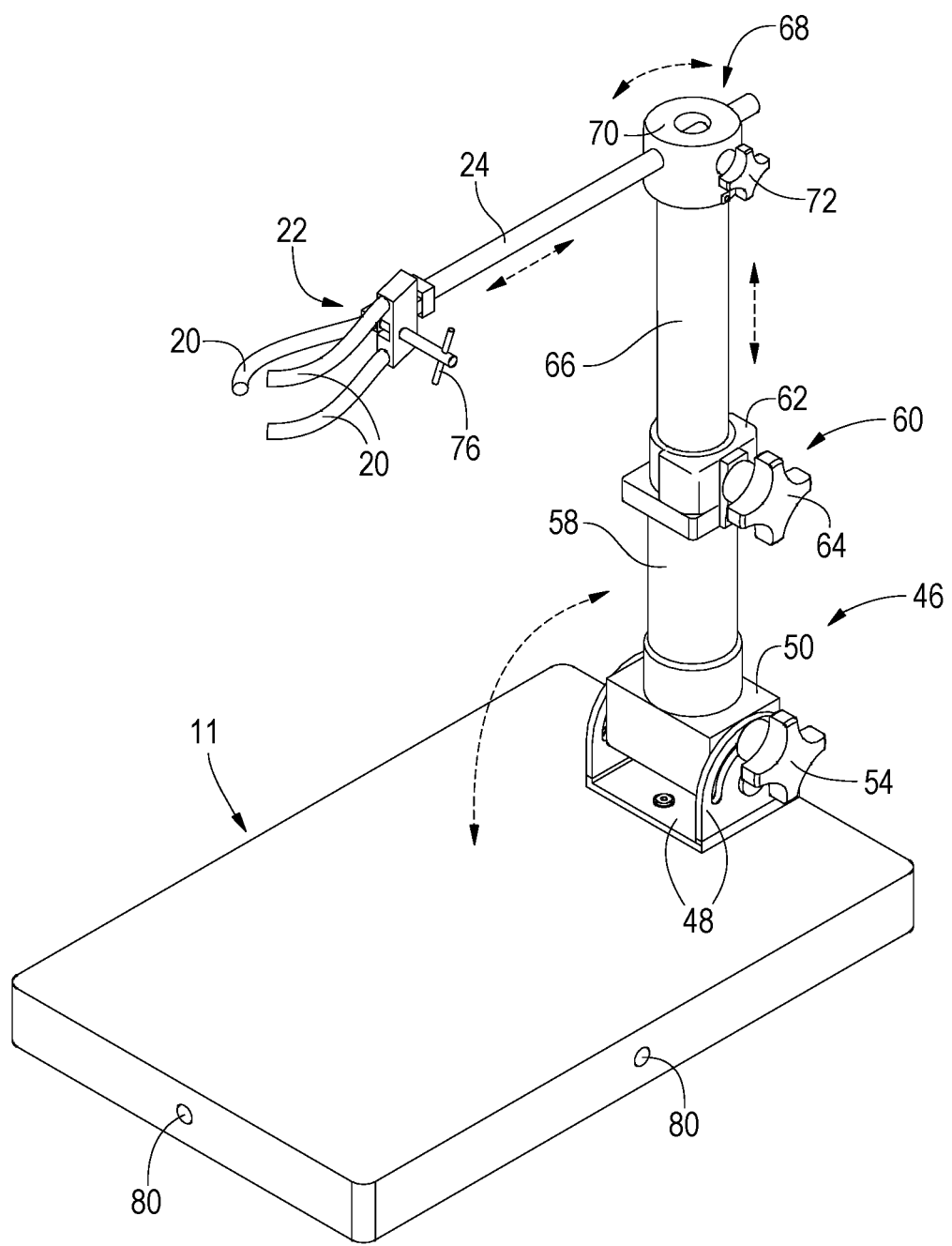
FIG. 2 is a perspective view of the present invention.
Figure 3:
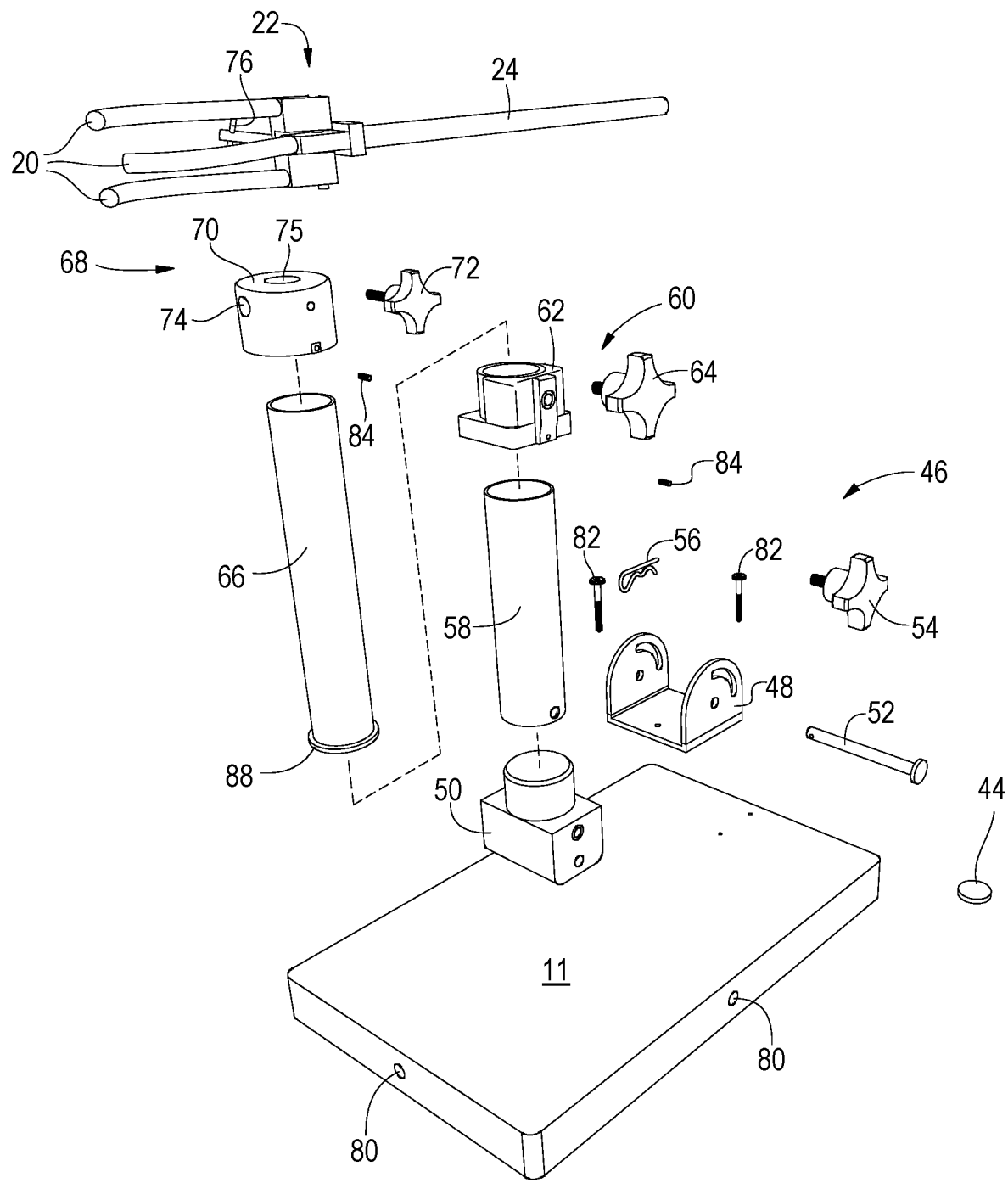
FIG. 3 is an exploded perspective view of the present invention.
Figure 4:
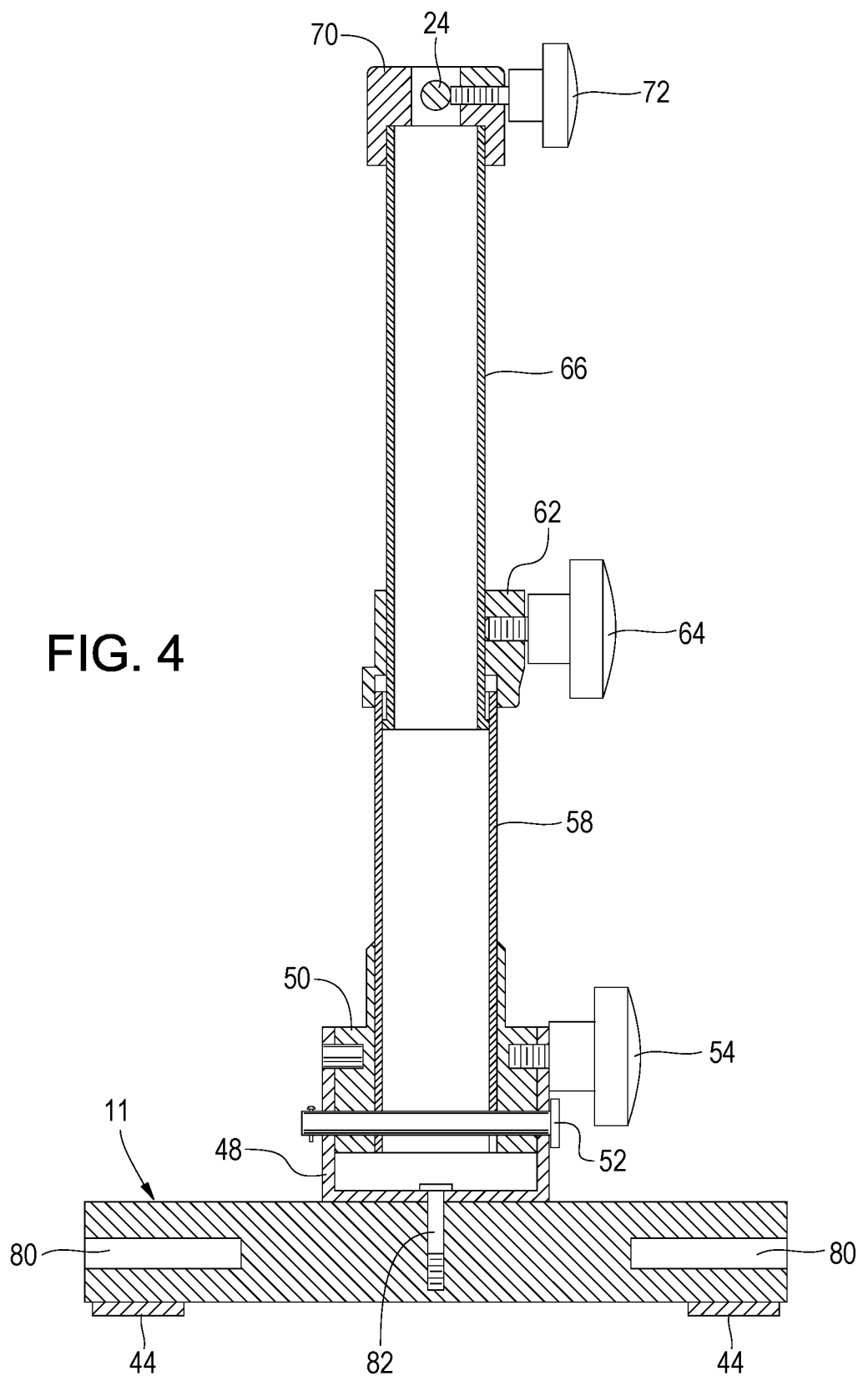
FIG. 4 is a cross sectional view of portions of the present invention.
Figure 5:
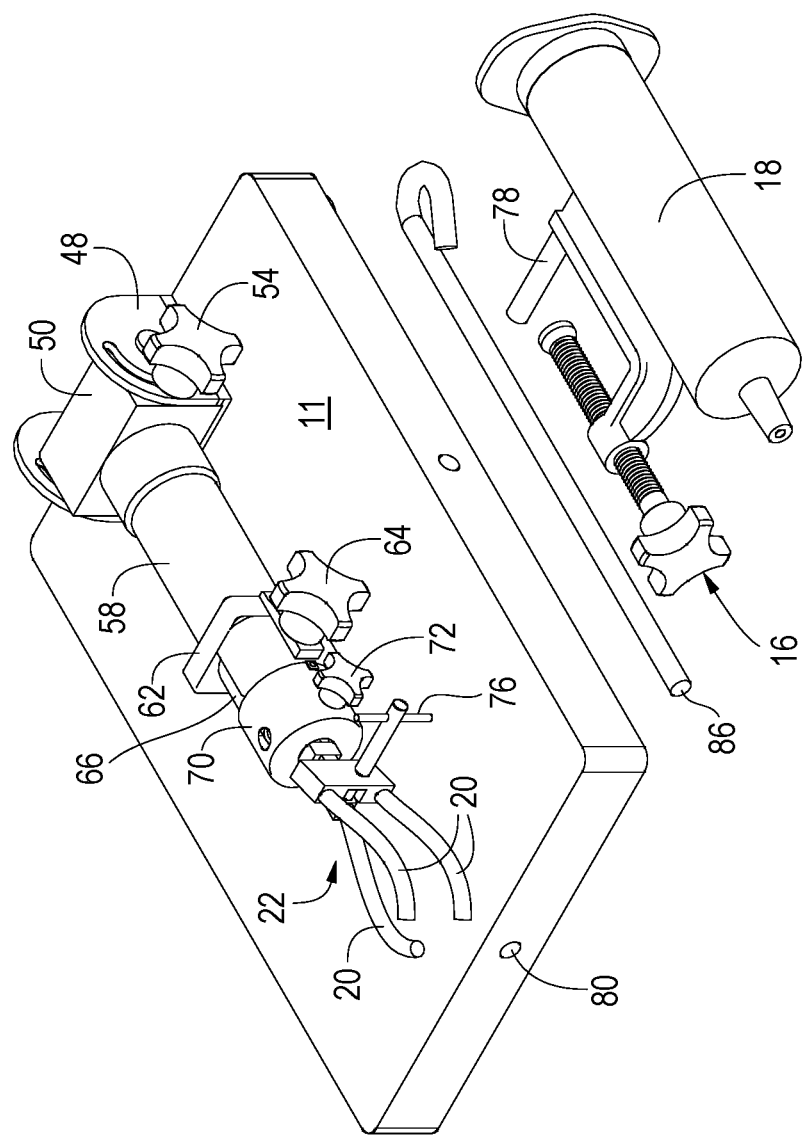
FIG. 5 is a perspective view showing the present invention in a folded position suitable for storage.

With regard to reference numerals used, the following numbering is used throughout the drawings.
- 10 present invention
- 11 base
- 12 top of table
- 14 table
- 16 optional stabilizing clamp
- 18 syringe
- 19 fluid food
- 20 jaws/fingers
- 22 adjustable clamp
- 24 arm
- 26 feeding tube extension
- 28 outlet connector port
- 30 inlet connector port
- 32 PEG tube/feeding tube
- 34 user
- 36 chair
- 38 hand
- 40 article
- 44 footpads
- 46 column mount assembly
- 48 column support bracket
- 50 column pivot coupler
- 52 column pivot pin
- 54 column tensioning knob
- 56 column pivot pin retaining clip
- 58 column lower tube section
- 60 extension locking collar assembly
- 62 extension locking collar
- 64 extension locking collar tensioning knob
- 66 column upper tube section
- 68 feed arm mount & storage assembly
- 70 feed arm mount/store coupler
- 72 feed arm coupler tensioning knob
- 74 hole/aperture
- 75 hole/aperture
- 76 adjustment handle
- 78 clamp rod
- 80 hole/aperture
- 82 M3 X25 mm flat allen head screw
- 84 set screws
- 86 IV/bulk bag feed arm
- 88 stop ring

DETAILED DESCRIPTION OF THE PREFERRED EMBODIMENT

The following discussion describes in detail at least one embodiment of the present invention. This discussion should not be construed, however, as limiting the present invention to the particular embodiments described herein since practitioners skilled in the art will recognize numerous other embodiments as well. For a definition of the complete scope of the invention the reader is directed to the appended claims. FIGS. 1 through 5 illustrate the present invention wherein an enteral feeding system is disclosed and which is generally indicated by reference number 10.

Turning to FIG. 1, therein is shown the present invention 10 being an enteral feeding device having a base 11 attached to a top 12 of a table 14 by means of an optional clamp 16 along with a syringe 18 containing fluid food 19 therein being held in the jaws 20 of a conventional clamp 22 disposed on an arm 24 with a feeding tube extension 26 having an outlet connector port 28 being connected to an inlet connector port 30 of a permanently installed PEG tube/feeding tube 32, or the like, of a user 34. A small adjustment handle 23 is shown on clamp 22 for adjusting the distance between the fingers 20. The user 34 is shown seated in a chair 36 wherein the present invention 10 allows the hands 38 to be free so that the user can hold an article 40 therein while at the same time receiving food 19 through PEG tube/feeding tube 32.

The present invention 10 is designed to facilitate Enteral Feeding (via PEG tube, G-tube, J-tube, J-G tube), whether by bolus or IV/bulk bag, in a manner that provides portability, flexibility, and stability for a user 34 with an Enteral feeding tube 32 and/or their caregiver. The device 10 sits stably on most tables 14 or like flat surfaces and includes an optional stabilizing clamp 16 to be attached when needed.

By way of general explanation and by reference to FIGS. 1-5, the present invention 10 is shown having a rectangular base 11 constructed of materials that meet U. S. Food and Drug Administration (FDA) guidelines for food handling purposes at room temperature and that are generally dishwasher safe. This applies to all materials used with the present invention 10. Attached to the bottom surface of the base 1 are four non-skid, non-marring foot pads 44 secured to the bottom surface by self-adhesive pads. The base 11 supports a column mount assembly 46 on the top surface of the base on the rear end portion, on centerline including a column lower tube section 58, a column support bracket 48, a column pivot coupler 50, a column pivot pin 52, a column tensioning knob 54 and a column pivot pin retaining clip 56. The column 58 is joined to a pivoting coupler 50 that allows the column to be placed in the upright "in-use" position perpendicular to the base 11 top surface, or in the storage position where it rests parallel to the base top surface. The column 58 can be locked in either position by use of a tensioning screw/knob 54. The lower section of the column 58 is formed of a round tube connected on its bottom end to both the pivoting coupler 50 and column mounting bracket 48 by a round pin 52 inserted through all components. An extension locking collar coupling assembly 60 including an extension locking collar 62, an extension locking collar tensioning knob 64 and a column upper tube section 66 is attached to the top of the lower column tube 58 and allows an upper column tube 66 to telescopically slide inside the lower column tube 58 and be extended to variable heights. The upper column tube 66 travel range is limited on the lower end by the bottom of the upper tube 66 resting on the pin 52 used to secure the lower column tube 58 to the pivot coupler 50 and bottom bracket 48. The upward range is constrained by a stop ring 88 built into the lower end of the upper tube 66 contacting an interior ledge within the extension coupling. The upper tube 66 is held in any position throughout its range by use of a tensioning screw/knob 64 of identical design to the knob 54 used for the pivot coupling 50.

At the top of the upper column tube 66 is a feed arm mount and storage assembly 68 including a feed arm mount/store coupler 70 and feed arm coupler tensioning knob 72. The assembly 68 is used for securing a feed arm 24 in either the "in-use" position or in the storage position. In its "in-use" position, the feed arm 24, which consists of a commercially available laboratory retort clamp 22 and rod 24, is inserted through a hole 74 in the vertical faces of the feed arm coupling 68 and secured in position, extending horizontally, at the appropriate extension length desired by the user 34. An additional hole/aperture 75 in provided in the top end of coupler 70 for receiving arm 24 when in the storage position. The feed arm 24 is secured by means of a tensioning screw/knob 72 that is similar, but not in-kind, to those used for the extension 64 and pivot couplings 54. While normally extending from back to front along the base centerline, the feed arm 24 can also be rotated in the horizontal plane. The upper column tube 66 and attached feed arm coupler 70 are designed to rotate 360 degrees for maximum flexibility in placement of the feed arm 24. This is accomplished by loosening the extension coupling tensioning screw/knob 64, turning the upper tube 66 in any direction to the desired position, then retightening the tensioning screw/knob 64.

At this point, for people practicing bolus feeding by pouring from a carton or other container, the user 34 would place a catheter syringe 18, typically 60 ml or greater, or similar vessel with a bottom tapered connection, into the retort arm adjustable jaws or fingers 20 and clamp the syringe/vessel 18 in place with the retort adjustment handle 76. The user 34 would then connect the enteral feeding tube 26 to the syringe/vessel 18 and their installed inlet feeding port 30, and then proceed to flush, feed, and/or administer medications as normal. Once feeding is complete, the syringe vessel 18 is removed for cleaning or disposal. To store the feed arm 24, it is removed from the feed arm coupler 70 and rotated to the vertical position with the retort "fingers" 20 in an upward position, and the rod 24 inserted into the hole 75 provided in the top surface of the feed arm coupling 70, lowering the rod into the column. The feed arm 24 is then secured in place by tightening the feed arm coupler tensioning screw/knob 72. At this point, the column 66 is ready to be collapsed to its shortest length by loosening the extension coupling tensioning screw/knob 64, lowering the upper tube completely, and retightening the intermediate or extension coupling tensioning screw/knob 64.

Next, the pivot coupler tensioning screw/knob 54 is loosened and the column assembly 46 is rotated until the column 58 is situated parallel to the top of the base 11, where the screw/knob 54 is retightened. For bulk or IV bag feeding, the process is the same as described above except the retort feed arm 24 is removed and the provided IV/bulk bag feed arm/holder 86 having a hook on one end is installed in its place in the same manner.

In situations where the user 34 may have physical or mental disabilities that could result in the feeding platform being overturned or disconnected from the feeding tube assembly, or where the table or other flat surface is inadequate, the optional stabilizing clamp 16 is provided. The clamp 16 is similar to a conventional c-clamp design that is commercially available and often referred to as a table edge clamp or "bessey" and consists of an upper jaw in the form of a round rod 78 connected to the lower jaw which contains the adjusting screw and handle. Clamping is accomplished by inserting the upper jaw rod 78 into a hole 80 in the material to be clamped, in this case the feeding platform base 11 and tightening the lower jaw adjusting screw against the underside of the supporting surface. The base 11 is designed with holes 80 in the front edge face and both side edge faces to allow the user 34 to position the platform along either the long or short axis orientation to best suit their situation. Also of note is that all couplings 50, 62, 70 and adjusting/tensioning screws/knobs 54, 64, 72 are designed to be ambidextrous; they can be easily rotated so that the adjusting mechanism is at its favored position for right or left handed users and all. All adjusting/tensioning screws/knobs 54, 64, 72 include a conventional male threaded screw portion on an end thereof.

The retort clamp 22 greatly increases the range of syringe/vessel 18 diameter that can be used for feeding because the related art is either fixed in the size syringe it can hold or can only adjust within a very small range. The base 11 is intentionally effectively large enough to provide a sufficient flat, stable surface for placing formula tetra packs, medication bottles/holders, and other supplies within easy reach of the user 34 and provides a serving plate-like feature for the enteral feeding materials and the related art does not address this need. The base 11 also is designed to allow the personalization of the present invention 10 through the application of art work by way of painting, decals, etchings, or other means so as to enhance the dining experience of user 34 and provide a more positive view of the feeding process.

Lines with arrowheads are sometimes placed on drawings to indicate potential movement/motion or direction of movement of an item illustrated in the drawing.

I claim:

1. A portable enteral feeding platform for use by a patient, comprising:
    a) a base comprising a solid flat member supporting a column assembly in a deployed upright position for feeding the patient and said column assembly in a storage position when not deployed for feeding the patient;
    b) a column pivot coupler mounted on said base adjacent one edge of said base;
    c) said column assembly when deployed for feeding extending up from said column pivot coupler, said column assembly having telescoping upper and lower sections, said upper and lower sections each having upper and lower ends, wherein said upright column is adjustable in height, said column pivot coupler allowing pivoting of said upright column assembly to fold down against an upper flat surface of said base when in said storage position;
    d) a feed arm coupler removably and rotatably attached to a top end of said upper section of said assembly;
    e) a feed arm extending horizontally from said feed arm coupler allowing positioning said feed arm in any direction while maintaining its horizontal orientation when said feeding platform is deployed;
    f) a clamp mounted on a distal end of said feed arm for holding a syringe containing fluid food for use by the patient;
    g) a feeding tube having a connector at a proximal end for attachment to said syringe and an outlet connector port on a distal end for attachment to a PEG tube/feeding tube on said patient;
    h) wherein only one hand of said patient is required to obtain feeding when desired; and
    i) wherein said enteral feeding platform is readily dismantled and folded on aid base for storage and relocation.

2. The enteral feeding platform of claim 1, further comprising a first adjustable tensioning knob disposed on said lower and of said lower section for locking said upright column into a user selected position.

3. The enteral feeding platform of claim 2, further comprising a second adjustable tensioning knob disposed on said feed arm coupler on said upper end of said upper section for locking said arm of said clamp into a user selected position.

4. The enteral feeding platform of claim 3, further comprising a third adjustable tensioning knob disposed between said first and second adjustable tensioning knob for locking said telescoping upper and lower sections into a user selected position.

5. The enteral feeding platform of claim 4, wherein said first, second and third adjustable tensioning knobs we each adapted to be mounted on either a left side or aright side of its respective sections so as to be used by either a right handed or a left handed patient.

6. The enteral feeding platform of claim 5, wherein said base is effectively large to stabilize said upright column in an upright position.

7. The enteral feeding platform of claim 6, wherein a top end of said upper end of said upper section has a hole therein, said hole for receiving said arm of said clamp therein when said upright column is in said storage position.

8. The enteral feeding platform of claim 7, wherein said clamp is adjustable for use with different sizes of syringes.

9. The enteral feeding platform of claim 8, further comprising a stabilizing clamp to permit said base to be secured to a flat surface.

10. The enteral feeding platform of claim 9, in which aid clamp comprises a pair of spaced fingers extending from an adjustment handle on said distal end of said feed arm, said spaced fine curved to grasp one side of said syringe, and a third finer extending from said adjustment handle to grasp an opposite side if said syringe, said adjustment handle having an adjustment member to tighten said fingers around said syringe to secure said syringe while in use.

11. A method of assembling and deploying for use an enteral feeding platform for use by a patient, comprising the steps of:
   a) providing a base comprising a flat solid platform for supporting the enteral feeding platform so as to free the hands of the patient;
   b) attaching a bottom end of a column in a pivot coupler mounted on said base adjacent one edge of said base, said column being pivotal between an upright position deployed for use in feeding said patient and a storage position in which said column is folded down against an upper flat surface of said base, said column having telescoping upper and lower sections ends, each upper and lower section having upper and lower ends, wherein the column is adjustable length;
   c) removably attaching a feed arm coupler to a distal end of said column when deployed in an upright position;
   d) removably attaching a proximal end of a feed arm to said feed arm coupler, said feed arm extending horizontally from said feed arm coupler allowing positioning of said feed arm in any direction while maintaining its horizontal orientation when said feeding platform is deployed;
   e) mounting a clamp on a distal end of said feed arm for holding a syringe containing fluid food for use by the patient; and
   f) attaching a connector on a proximal end of a feeding tube to said syringe;
   g) attaching an outlet connector on a distal end of said feeding tube to a PEG tube/feeding tube on said patient for feeding said patient; and
   h) upon termination of feeding removing said feed arm from said feed arm coupler and rotating said column into said storage position on said base.

12. The method of claim 11, further comprising the step of providing a first adjustable tensioning knob on the lower end of the lower section for locking the upright column into a user selected position.

13. The method of claim 12, further comprising the step of providing a second adjustable tensioning knob on the upper end of the upper section for locking the arm of the clamp into a user selected position.

14. The method of claim 13, further comprising the step of providing a third adjustable tensioning knob between the first and second adjustable tensioning knobs for locking the telescoping upper and lower sections into a user selected position.

15. The method of claim 14, adapting the first, second and third adjustable tensioning knobs to be mounted on either a left side or a right side of its respective sections so as to be used by either a right handed or a left handed patient.

16. The method of claim 15, sizing the base to be effectively large to stabilize the column in an upright position.

17. The method of claim 16, further comprising the step of providing a hole in a top end of the upper and of the upper section for receiving the arm of the clamp therein when in the storage position.

18. The method of claim 17, adjusting the size of the clamp for use with different sizes of syringes.

19. The method of claim 18, further comprising the step of providing a stabilizing clamp to permit the base to be secured to a flat surface.

20. The method or claim 19, further comprising the step of providing a bulk beg feed arm for mounting on the upper end of the upper section of the upright column, the bulk bag feed arm having a hook thereon.

\* \* \* \* \*